(12) United States Patent
Zhang et al.

(10) Patent No.: US 9,855,073 B2
(45) Date of Patent: Jan. 2, 2018

(54) CIRCUMCISION STAPLER

(71) Applicant: Shoufu Zhang, Changde (CN)

(72) Inventors: Shoufu Zhang, Changde (CN);
Lunxiang Zhang, Changde (CN)

(73) Assignee: Shoufu Zhang, Changde, Hunan (CN)

( * ) Notice: Subject to any disclaimer, the term of this patent is extended or adjusted under 35 U.S.C. 154(b) by 103 days.

(21) Appl. No.: 14/706,607

(22) Filed: May 7, 2015

(65) Prior Publication Data

US 2015/0313625 A1  Nov. 5, 2015

Related U.S. Application Data

(63) Continuation of application No. PCT/CN2013/086803, filed on Nov. 8, 2013.

(30) Foreign Application Priority Data

Nov. 8, 2012 (CN) .......................... 2012 1 0442303
Mar. 6, 2013 (CN) .......................... 2013 1 0071003
Apr. 8, 2013 (CN) .......................... 2013 1 0118992
May 17, 2013 (CN) ..................... 2013 2 0271197 U

(51) Int. Cl.
*A61B 17/32* (2006.01)
*A61B 17/326* (2006.01)

(52) U.S. Cl.
CPC .................. *A61B 17/326* (2013.01)

(58) Field of Classification Search
CPC .................................................. A61B 17/326
USPC ................................................ 606/118, 157
See application file for complete search history.

(56) References Cited

U.S. PATENT DOCUMENTS

| 4,491,136 A | 1/1985 | LeVeen |
| 5,163,943 A * | 11/1992 | Mohiuddin .......... A61B 17/326 227/175.1 |
| 5,269,788 A | 12/1993 | Nelson, III |
| 2011/0098718 A1* | 4/2011 | Shang .................. A61B 17/326 606/118 |
| 2011/0178528 A1* | 7/2011 | Kostrzewski ........ A61B 17/326 606/118 |

(Continued)

FOREIGN PATENT DOCUMENTS

| CN | 2424748 | 3/2001 |
| CN | 2707199 | 7/2005 |

(Continued)

OTHER PUBLICATIONS

First Office Action and Search Report issued in Chinese Patent Application 201210442303.X, dated Apr. 1, 2014, 5 pages.

(Continued)

*Primary Examiner* — Katherine M Shi
(74) *Attorney, Agent, or Firm* — Hamre, Schumann, Mueller & Larson, P.C.

(57) ABSTRACT

A circumcision stapler comprises three parts: an upper stapler, a lower stapler and a rivet fastening and regulating member, wherein an outer knife, an inner knife anti-skidding groove, an anti-skidding bulge, a frenum protecting part and a plurality of rivet holes with same sizes are arranged on the upper stapler; an inner knife, an outer knife anti-skidding groove, an anti-skidding bulge, a frenum protecting part and a plurality of rivet holes with same sizes, and a rivet fastening column are arranged on the lower stapler.

8 Claims, 19 Drawing Sheets

(56) References Cited

U.S. PATENT DOCUMENTS

| | | | |
|---|---|---|---|
| 2012/0277759 A1* | 11/2012 | Shang | A61B 17/326 606/118 |
| 2012/0303040 A1* | 11/2012 | Johnson | A61B 17/326 606/118 |
| 2012/0303041 A1 | 11/2012 | Marczyk et al. | |
| 2013/0144304 A1* | 6/2013 | Shang | A61B 17/326 606/118 |

FOREIGN PATENT DOCUMENTS

| | | |
|---|---|---|
| CN | 2848142 | 12/2006 |
| CN | 1919152 | 2/2007 |
| CN | 201683982 | 12/2010 |
| CN | 201710420 | 1/2011 |
| CN | 102028520 | 4/2011 |
| CN | 201847738 | 6/2011 |
| CN | 201905975 | 7/2011 |
| CN | 102384089 | 3/2012 |
| CN | 102743211 | 10/2012 |
| CN | 202604965 | 12/2012 |
| CN | 102895018 | 1/2013 |
| CN | 102935007 | 2/2013 |
| CN | 102940520 | 2/2013 |
| CN | 103099655 | 5/2013 |
| CN | 103169527 | 6/2013 |
| CN | 203089300 | 7/2013 |
| CN | 203138627 | 8/2013 |
| CN | 203244437 | 10/2013 |
| SU | 1232234 | 5/1986 |
| WO | 2007028378 | 3/2007 |
| WO | 2009114529 | 9/2009 |

OTHER PUBLICATIONS

First Office Action and Search Report issued in Chinese Patent Application 201310071003.X, dated Jul. 21, 2014, 6 pages.
First Office Action and Search Report issued in Chinese Patent Application 20130118992.3, dated Jul. 3, 2014, 6 pages.
International Search Report, dated Feb. 20, 2014 in the corresponding PCT application No. PCT/CN2013/086803, 9 pages.

* cited by examiner

CIRCUMCISION STAPLER

TECHNICAL FIELD

The present application relates to a circumcision stapler for foreskin of penis of males, belonging to the technical field of medical apparatuses and instruments.

BACKGROUND

Functions of circumcision in avoiding balanitis and urethritis caused by redundant foreskin and phimosis, decreasing venereal diseases, reducing spread of AIDS and preventing carcinoma of penis have been accepted widely in the medical field. With continuous innovation of modern circumcision, the simplicity, safety and minimally invasive surgery quality of the circumcision are greatly improved. At present, in all circumcisions, all circumcision methods have their own advantages, which provides more choices for patients and doctors. However, each circumcision method has serious defects: 1. the conventional circumcision can completely protect the frenum and enable the glans penis to normally contract and relax, but has the defects of long duration of operation, large amount of bleeding, strong aching feeling, needs of stopping bleeding, suturing, taking out stitches, changing fresh dressing for a wound, performing transfusion after operation, and the like; 2. a disposable circumcision instrument (including a disposable circumcision anastomosis instrument) commonly used clinically at present can enable the duration of operation to be shortened, the amount of bleeding to be less and the aching feeling to be small, does not need to stop bleeding, suture, take out stitches, change fresh dressing for a wound, and perform the transfusion after operation, but still can not completely meet the requirement of clinical medicine, for example, Patent Publication No. CN2424748 entitled 'foreskin cerclage device' and Chinese Patent Application Number CN201710420U entitled 'circumcision positioner and disposable circumcision stapler' and the like, glans penis, frenum, coronary sulcus and tissues around them can not be visually observed during operation, and further can not be observed after operation, which causes a result that the circumcision is a blind operation basically, however, unexpected consequences may be incurred; another circumcision device, for example, Patent Publication No. CN201683982U entitled 'circumcision device', although glans penis, frenum, coronary sulcus and tissues around them can be seen, length of the frenum and relevant tissues can not be completely reserved, which causes a result that the glans penis can not normally contract and relax, and the frenum may be broken by pulling, leading to bad consequences. Edema of frenum, foreskin and tissues around them are observed after circumcision, which will cause the healing time after operation to be prolonged and the pain of patients to be exacerbated, and result in escharosis, chronic inflammation, hyperplasia and incrassation in inner plate and outer plate of the foreskin after operation, impacting sexual life, and bring pain and anxiety for patients; meanwhile, considerable troubles are brought for doctors, especially for children and senile patients; because end-piece of urine of such patients can not be completely discharged from urethral orifices such that the urine is easily immersed into the wound, removing circumcision device might be distressing to patients and the patients is terrified, and wounds are difficult to be healed after the circumcision device is removed.

In addition, a disposable circumcision loop ligature instrument, a disposable circumcision anastomosis instrument and the like which are commonly used clinically at present can enable the duration of operation to be shortened, the amount of bleeding to be reduced and the aching feeling to be less intense, do not need to stop bleeding, suture, take out stitches, and perform the transfusion after operation, but still can not completely meet the requirement of clinical medicine, the main reasons are as follows: no regulating member is arranged on a circumcision stapler or the regulating member is arranged improperly, clinical requirements can not be completely met when loop ligature lines or outer loops are removed, especially for children and senile patients, removing the circumcision device might be distressing and unacceptable to the patients after they use the device; meanwhile, considerable troubles are brought to the doctors.

In addition, no connecting member is arranged on a circumcision device in the prior art or the connecting member is arranged improperly, clinical requirements can not be completely met when the outer loops are removed, especially for children and senile patients, removing the circumcision device might be distressing and unacceptable to the patients after they use the circumcision device; meanwhile, considerable troubles are brought to the doctors.

In the prior art, a foreskin circumcising method involves inserting the cylindrical ring (also called the first ring) of the lower ring stapler within the foreskin of male patient (e.g. when he lies on his back during a circumcision operation), radially clamping foreskin against circumference of the first ring by the upper ring stapler and axially (or annually) cutting the foreskin against the first ring.

SUMMARY OF THE APPLICATION

In order to overcome the above defects of an existing circumcision device, the present application provides a novel disposable foreskin circumcision stapler kit (also known as a circumcision device), which is used for fundamentally changing the defects that a conventional circumcision is lack of standardization and has no uniform standard devices, so as to achieve the purposes of being accurate in operation positioning, short healing time after operation, being capable of preventing edema, preventing infection and relieving patient's pain.

To solve the technical problems, for the defects of various operation methods, the inventor performed dedicated researches and experiments for many years in extensive clinical works for years, adopted a positioning, compound, multi-facet and curved cutting method according to features of the reproductive organ of males, and finally designed multiple novel disposable circumcision staplers based on the prior art.

According to a first implementation of the present application, the present application provides:

1. A circumcision stapler kit (also known as a circumcision device or a foreskin circumcision anastomat or a foreskin circumciser), the circumcision stapler kit comprises three parts: an upper ring stapler having an (or two) outer ring-knife(s) on its lower-and-outer side circumference, a lower ring stapler having an inner ring-knife on its upper-and-inner side circumference and a rivet fastening and regulating member, and is characterized in that:

An (or two) outer ring-knife(s), an anti-skidding groove into which the inner ring-knife of the lower ring stapler will be fitted, optional anti-skidding bulges on the edge of the outer ring-knife(s), a frenum protecting part (also called the first frenum protecting part) which is a part of the ring of the upper ring stapler and a plurality of rivet holes with same sizes are arranged on/in the upper ring stapler, wherein a foreskin-cutting plane of the outer ring-knife's part which is in the frenum protecting part of the upper ring stapler and a foreskin-cutting plane of the remaining main part of the outer ring-knife are not in the same horizontal plane (i.e. the former plane deviates from the later to the base of man's penis) when the main body of the upper ring stapler be placed horizontally, and wherein the frenum protecting part of the upper ring stapler is (or has) a ring-radial-outward semi-elliptical or triangular radian portion (i.e., V-shaped protrusion or U-shaped protrusion, for fitting to or engaging with the shape of below-mentioned frenum protecting part of a lower ring stapler);

An inner ring-knife, an anti-skidding groove(s) into which the outer ring-knife(s) of the upper ring stapler will be fitted, rivet holes, a rivet fastening column, optional anti-skidding bulges on the edge of the inner ring-knife(s) and a frenum protecting part (also called the second frenum protecting part) which is a part of the ring of the lower ring stapler are arranged on/in the lower ring stapler, wherein a foreskin-cutting plane of the inner ring-knife's part which is in the frenum protecting part of the lower ring stapler and the foreskin-excision plane of the remaining main part of the inner ring-knife are not in the same horizontal plane (i.e. the former plane deviates from the later to the base of man's penis) when the main body of the lower ring stapler be placed horizontally, and wherein the frenum protecting part of the lower ring stapler is (or has) a ring-radial-outward semi-elliptical or triangular radian portion (i.e., V-shaped protrusion or U-shaped protrusion, for accommodation of the frenum) and corresponds to (or engage with) the radian of the frenum protecting part of the upper ring stapler; and A rivet, a rivet boss, a rivet lead screw part, a rivet cap and a rivet screw nut are arranged on the rivet fastening and regulating member; the upper ring stapler and the lower ring stapler are assembled as a kit by the rivets penetrating through the rivet holes of the upper ring stapler, the rivet holes of the lower ring stapler, the rivet holes or a lower ring stapler fastening columns and the rivet holes of a snap ring; wherein the outer ring-knife(s) of the upper ring stapler engage(s) with the outer ring-knife's anti-skidding groove(s) on the lower ring stapler, the inner ring-knife of the lower ring stapler engages with the inner ring-knife's anti-skidding groove on the upper ring stapler, and optionally further by means of the fixation provided by the anti-skidding bulges, the upper ring stapler and the lower ring stapler are (or can be) tightly connected so as to engage with and circumcise foreskin.

2. The rivet holes of the upper ring stapler described in the above item 1 penetrate through the upper ring stapler, consist of a plurality of circular holes with same sizes, and are distributed on the corresponding main plane of the upper ring stapler; the outer ring-knife of the upper ring stapler is positioned at the outer edge of the outside of the upper ring stapler, is an auxiliary excision knife, is an annular three-dimensional multi-faced excision knife, and is a complete annular three-dimensional multi-faced arc-shaped knife; the inner ring-knife's anti-skidding groove of the upper ring stapler is a complete concave groove and (its configure) is parallel to the outer ring-knife; a certain gap is arranged between the outside of the concave groove and the outer ring-knife of the upper ring stapler, and in this gap there are several narrow hollow slits on the upper side of the upper ring stapler, these narrow hollow slits be called as a outer (i.e., opposite to the base of man's penis) excision holes (slits); optionally the anti-skidding bulges of the upper ring stapler are uniform dotted bulges positioned on an outer ring-knife edge of the upper ring stapler.

3. The frenum protecting part of the upper ring stapler described in the above item 1. or 2. is positioned at the lower side of the upper ring stapler when the circumcision stapler kit be put on man's penis with the frenum direction being downward, the frenum protecting part extends forward a distance along the frenum length direction with penis as the center, and the frenum protecting part of the upper ring stapler is (or has) a ring-radial-outward semi-elliptical or triangular radian portion (i.e., V-shaped protrusion or U-shaped protrusion); the top end of the semi-elliptical or triangular radian portion is provided with a frenum positioning column, or reserved with a frenum positioning opening;

4. The rivet holes of the lower ring stapler described above penetrate through the lower ring stapler (as a lower member), and consist of a plurality of circular holes which have same sizes and correspond to those rivet holes of the upper ring stapler; the rivet fastening columns are hollow tubular columns formed by the rivet holes which extend outwards from a side of the main plane of ring and this side faces toward to the base of a penis, the distal end of each rivet fastening column is opened so that the tubular column is divided into left part and right part, nap ring(s) (i.e. fastening ring(s)s) is/are arranged in each hollow tubular column; the inner ring-knife of the lower ring stapler is positioned on the upper-and-inner side circumference of the lower ring stapler, is a main excision knife, and is a complete annular three-dimensional excision knife having a cambered edge over the frenum protecting part; the outer ring-knife's anti-skidding groove of the lower ring stapler is a complete concave groove, a certain gap is arranged between the inside of the concave groove and the inner ring-knife of the lower ring stapler, and in this gap there are several narrow hollow slits on the lower side of the lower ring stapler, these narrow hollow slits be called as a inner (i.e., facing to the base of man's penis) excision holes (slits) and correspond to those outer excision holes (slits) of the upper ring stapler; optionally the anti-skidding bulges of the lower ring stapler are uniform dotted bulges positioned on an inner ring-knife edge of the lower ring stapler;

5. The frenum protecting part of the lower ring stapler is positioned at the lower side of the lower ring stapler when the circumcision stapler kit be put on man's penis with the frenum direction being downward, the frenum protecting part extends forward a distance (sufficient to completely reserve the length of the frenum) along the frenum length direction with penis as the center, and the frenum protecting part of the upper ring stapler is (or has) a ring-radial-outward semi-elliptical or triangular radian portion (i.e., V-shaped protrusion or U-shaped protrusion); the top end of the semi-elliptical or triangular radian portion is provided with a hollow tubular column which corresponds to the positioning column of the upper stapler;

6. The rivet in the rivet fastening and regulating member comprises a rivet boss, a rivet lead screw part and a rivet cap, the rivet boss is positioned at the front end of the rivet and is formed by two succecive boss parts with different sizes, with a spacing therebetween; the rivet lead screw part is positioned at the rear end of the rivet and is threaded; the rivet cap is positioned at the tail end of the rivet lead screw part to prevent a screw nut from slipping; the rivet screw nut part is a gear-shaped or polygonal screw nut, and matches with the rivet lead screw part in a nesting manner.

According to a second implementation of the present application, the present application provides a frenum protecting part of a circumcision stapler, which is used for completely reserving the length of the frenum and relevant tissues, is suitable for patients with different frenum lengths, enables the glans penises of the patients to be normally contracted, and avoids accidents of bad consequences caused by breaking the frenum.

To solve the technical problems, for the defects of various operation manners, the inventor performed dedicated researches and experiments for many years in extensive clinical works for years, adopted a positioning compound multi-excision plane and arc-excision method according to features of the reproductive organ of males, and finally designed a frenum protecting part of a novel circumcision ring stapler based on the prior art. The frenum protecting part comprises a frenum protecting part of the upper ring stapler and a frenum protecting part of the lower ring stapler, wherein the frenum protecting part of the upper ring stapler is formed by connecting a left semicircular member and a right semicircular member by means of a connecting member, the frenum protecting part of the upper ring stapler and the frenum protecting part of the lower ring stapler are assembled into a whole by means of the fastening and regulating member for excising the foreskin;

the frenum protecting part is characterized in that:

1. the frenum protecting part which is a part of the ring of the upper ring stapler is arranged on a single circumcision knife or two circumcision knives of the upper ring stapler, the excision plane in which the frenum protecting part of the upper ring stapler is located and a main body excision plane of the upper ring stapler are on the same horizontal plane when the main body of the upper ring stapler be placed horizontally and the frenum protecting part is provided with or is a V-shaped protrusion as a ring-radial-outward semi-elliptical or triangular radian portion that is protruded outward in a direction perpendicular to the frenum length direction; or the excision plane in which the frenum protecting part of the upper ring stapler is located and the main body excision plane of the upper ring stapler are not on the same horizontal plane when the main body of the upper ring stapler be placed horizontally and the frenum protecting part is provided with or is a V-shaped protrusion as a ring-radial-outward semi-elliptical or triangular radian portion that is protruded outward in a direction perpendicular to the frenum length direction, and still, the main plane of the V-shaped protrusion is parallel to a main plane of a frenum protecting part of the lower ring stapler;

2. a frenum protecting part is also arranged on the lower ring stapler and which is a part of the ring of the lower ring stapler, the excision plane in which the frenum protecting part of the lower ring stapler is located and the main body excision plane of the lower ring stapler are on the same horizontal plane when the main body of the lower ring stapler be placed horizontally and this frenum protecting part is provided with or is a V-shaped protrusion as a ring-radial-outward semi-elliptical or triangular radian portion that is protruded outward in a direction perpendicular to the frenum length direction; or the excision plane in which the frenum protecting part of the lower ring stapler is located and the main body excision plane of the lower ring stapler are not on the same horizontal plane when the main body of the lower ring stapler be placed horizontally and this frenum protecting part is provided with or is a V-shaped protrusion as a ring-radial-outward semi-elliptical or triangular radian portion that is protruded outward in a direction perpendicular to the frenum length direction, and still, the main plane of this V-shaped protrusion of lower ring stapler is parallel to the main plane of the frenum protecting part of the upper ring stapler (when the lower ring stapler and the upper ring stapler are assemblied into a whole).

The second implementation of the present application may also be summarized as follows:

FIG. 9. A frenum protecting part of a circumcision stapler comprises a frenum protecting part of the upper ring stapler and a frenum protecting part of the lower ring stapler, wherein the frenum protecting part of the upper ring stapler is formed by connecting a left semicircular member and a right semicircular member by means of a connecting member, the frenum protecting part of the upper ring stapler and the frenum protecting part of the lower stapler are assembled into a whole by means of the fastening and regulating member for excising the foreskin; the frenum protecting part is characterized in that: the frenum protecting part which is a part of the ring of the upper ring stapler is arranged on a single circumcision knife or two circumcision knives of the upper ring stapler, the excision plane in which the frenum protecting part of the upper ring stapler is located and a main body excision plane of the upper ring stapler are on the same horizontal plane when the main body of the upper ring stapler be placed horizontally and the frenum protecting part is provided with or is a V-shaped protrusion as a ring-radial-outward semi-elliptical or triangular radian portion that is protruded outward in a direction perpendicular to the frenum length direction; or the excision plane in which the frenum protecting part of the upper ring stapler is located and the main body excision plane of the upper ring stapler are not on the same horizontal plane when the main body of the upper ring stapler be placed horizontally and the frenum protecting part is provided with or is a V-shaped protrusion as a ring-radial-outward semi-elliptical or triangular radian portion that is protruded outward in a direction perpendicular to the frenum length direction, and still, the main plane of the V-shaped protrusion is parallel to a main plane of a frenum protecting part of the lower ring stapler (when the lower ring stapler and the upper ring stapler are assemblied into a whole).

FIG. 10. The frenum protecting part described above, wherein a frenum protecting part is also arranged on the lower ring stapler and which is a part of the ring of the lower ring stapler, the excision plane in which the frenum protecting part of the lower ring stapler is located and the main body excision plane of the lower ring stapler are on the same horizontal plane when the main body of the lower ring stapler be placed horizontally and this frenum protecting part is provided with or is a V-shaped protrusion as a ring-radial-outward semi-elliptical or triangular radian portion that is protruded outward in a direction perpendicular to the frenum length direction; or the excision plane in which the frenum protecting part of the lower ring stapler is located and the main body excision plane of the lower ring stapler are not on the same horizontal plane when the main body of the lower ring stapler be placed horizontally and this frenum protecting part is provided with or is a V-shaped protrusion as a ring-radial-outward semi-elliptical or triangular radian portion that is protruded outward in a direction perpendicular to the frenum length direction, and still, the main plane of this V-shaped protrusion of lower ring stapler is parallel to the main plane of the frenum protecting part of the upper ring stapler (when the lower ring stapler and the upper ring stapler are assemblied into a whole).

According to a third implementation of the present application, the present application provides a regulating member of a novel disposable circumcision stapler, which is used for adapting to demands of different patients, facilitating the accurate positioning and operation of doctors, is easily accepted by recipients due to no pain when the device is removed, and is easily operated by the doctors.

To solve the technical problems, for the defects of various operation manners, the inventor performed dedicated researches and experiments for many years in extensive clinical works for years, adopted a positioning, combined, multi-excision plane type and arc-excision mode method according to features of the reproductive organs of males, and finally designed a regulating member of a novel circumcision stapler based on the prior art. The regulating member of the circumcision stapler comprises a rivet, a regulating spring, a boss for regulating foreskin (the boss is used when need to regulate foreskin), a boss for foreskin excision (this boss is used when need to excise foreskin), a rivet channel, a spring channel, a spring base, a rivet boss base, a regulating member wall and a rivet expanding notch, and is characterized in that: 1, the upper ring stapler is designed to be composed of two irregular semicircular rings, one ends of the two semicircular rings where the frenum is located are connected by means of a connecting member, the another ends i.e. opening ends of the two semicircular rings are connected by means of the regulating member under the action of the rivet and the regulating spring; the regulating member is arranged at the ring-radial-outside surface of the two semicircular rings of the upper ring stapler and on both opening ends when the two semicircular rings be assembled as the upper ring stapler, the regulating member is provided with the regulating member wall, the rivet channel, the spring channel, the spring base, the rivet boss base and the rivet expanding notch. 2, The regulating member of the upper ring stapler is connected by the rivet, the foreskin is excised under the action of the spring, and the rivet comprises a rivet column, a rivet cap, a boss for regulating foreskin and a boss for foreskin excision.

The third implementation of the present application may be also summarized as follows:

FIG. 13. The regulating member of the disposable circumcision stapler comprises a rivet, a regulating spring, a boss for regulating foreskin, a boss for foreskin excision, a rivet channel, a spring channel, a spring base, a rivet boss base, a regulating member wall and a rivet expanding notch, wherein the upper ring stapler is designed to be composed of two irregular semicircular rings, one ends of the two semicircular rings where the frenum is located are connected by means of a connecting member, the another ends i.e. opening ends of the two semicircular rings are connected by means of the regulating member under the action of the rivet and the regulating spring; the regulating member is arranged at the ring-radial-outside surface of the two semicircular rings of the upper ring stapler and on both opening ends when the two semicircular rings be assembled as the upper ring stapler, the regulating member is provided with the regulating member wall, the rivet channel, the spring channel, the spring base, the rivet boss base and the rivet expanding notch.

FIG. 14. The regulating member of the disposable circumcision stapler described in the above FIG. 13, wherein the regulating member of the upper ring stapler is connected by means of the rivet, the foreskin is excised under the action of the spring, as well as the rivet comprises a rivet column, a rivet cap, a boss for regulating foreskin and a boss for excising foreskin, and the trunk (i.e. central main section) of the rivet has a cylindrical shape, a square column shape, or a cylindrical and square column mixed shape.

FIG. 15. The regulating member of the disposable circumcision stapler described in the above FIG. 13, wherein the spring is a tower type (i.e. circular cone shape) compression spring or scroll compression spring.

According to a fourth implementation of the present application, the present application provides a connecting member of a novel disposable circumcision stapler, which is used for adapting to demands of different patients, facilitating the accurate positioning and operation of doctors, is easily accepted by recipients due to no pain when the device is removed, and is easily operated by the doctors.

To solve the technical problems, for the defects of various operation manners, the inventor performed dedicated researches and experiments for many years in extensive clinical works for years, adopted a positioning compound multi-excision plane and arc-excision method according to features of the reproductive organ of males, and finally designed a connecting member of a novel circumcision stapler based on the prior art.

The connecting member of the disposable circumcision stapler is arranged at one ends of two irregular semicircular upper ring staplers where the frenum protecting parts are located, or arranged at any position of the upper stapler, and is connected movably into a whole, wherein an upper connecting ring consisting of an upper connecting hole and an upper connecting hole wall and a lower connecting ring consisting of a lower connecting hole and a lower connecting hole wall are arranged at one sides of the two semicircular rings of the upper stapler where the frenum protecting part is located; a middle connecting ring consisting of a middle connecting hole and a middle connecting hole wall is arranged at the other sides of the two semicircular rings of the upper stapler; the upper connecting ring, the middle connecting ring and the lower connecting ring are equal in inner diameter and outer diameter, the height of the upper connecting ring and the lower connecting ring is smaller than that of the middle connecting ring, or heights of the upper connecting ring, the middle connecting ring and the lower connecting ring are equal; the middle connecting ring is embedded and clamped between the upper connecting ring and the lower connecting ring; a connecting shaft column is inserted in inner holes of the upper connecting ring, the middle connecting ring and the lower connecting ring in a penetrating manner, and is composed of a connecting shaft cap and a connecting shaft column connected with the connecting shaft cap into a whole.

The connecting shaft column reaches a lower connecting shaft cap recess of the lower connecting hole through the lower connecting hole, the middle connecting hole, the upper connecting hole and the connecting shaft cap, at this moment, the connecting shaft cap is level with the outer side surface of the lower connecting hole; the connecting shaft column is positioned in an upper connecting shaft cap recess of the upper connecting hole, and finally the front end of the connecting shaft column is cauterized flatly by using a dedicated screw cap end socket or using soldering iron.

The fourth implementation of the present application may also be summarized as follows:

FIG. 20. The connecting member of the disposable circumcision stapler is arranged at one ends of two irregular semicircular upper staplers where the frenum protecting part is located, or arranged at any position of the upper stapler, and is connected movably into a whole, wherein an upper connecting ring consisting of an upper connecting hole and an upper connecting hole wall and a lower connecting ring consisting of a lower connecting hole and a lower connecting hole wall are arranged at one sides of the two semicircular staplers where the frenum protecting part is located; a middle connecting ring consisting of a middle connecting hole and a middle connecting hole wall is arranged at the other sides of the two semicircular staplers; the upper connecting ring, the middle connecting ring and the lower connecting ring are equal in inner diameter and outer diameter, the height of the upper connecting ring and the lower connecting ring is smaller than that of the middle connecting ring, or heights of the upper connecting ring, the middle connecting ring and the lower connecting ring are equal; and the middle connecting ring is embedded and clamped between the upper connecting ring and the lower connecting ring; a connecting shaft column is inserted in inner holes of the upper connecting ring, the middle connecting ring and the lower connecting ring in a penetrating manner, and is composed of a connecting shaft cap and a connecting shaft column connected with the connecting shaft cap into a whole.

FIG. 21. The connecting member described above, wherein the connecting shaft column reaches a lower connecting shaft cap recess of the lower connecting hole through the lower connecting hole, the middle connecting hole, the upper connecting hole and the connecting shaft cap, at this moment, the connecting shaft cap is level with the outer side surface of the lower connecting hole; the connecting shaft column is positioned in an upper connecting shaft cap recess of the upper connecting hole, and finally the front end of the connecting shaft column is cauterized flatly by using a dedicated screw cap end socket or using soldering iron.

According to a fifth implementation of the present application, the present application provides a circumcision device comprising the upper stapler, the lower stapler, the frenum protecting part, the regulating member and the connecting member.

According to a sixth implementation of the present application, the present application provides a circumcision stapler (or circumcision device) for man's foreskin which comprises an outer stapler and a circular inner ring stapler B, with one side facing the base of penis as a front surface and one side away from the base of penis as a back surface when the circumcision device is used, wherein the outer ring stapler comprises two semicircular members A1 and A2, respective one ends (that is, connecting ends) of the two semicircular members A1 and A2 are connected by means of a connecting member 505 and two fastening members 501 and 502 suitable for butting joint fastening or pairing fastening are respectively arranged on outer surfaces of respective other ends (that is, one ends opposite to the connecting member, or known as fastening ends) of the two semicircular members A1 and A2, semi-arc-shaped circumcision knives C1 and C2 or semi-arc-shaped circumcision knives C1 and C2 (simply referred to as inner knives C1 and C2 or supplementary knives) at the inner side or near side (one side close to the base of penis) and semi-arc-shaped circumcision knives D1 and D2 (simply referred to as outer knives D1 and D2 or main knives) at the outer side or far side (one side far away from the base of penis) are respectively arranged on the inner surfaces of the two semicircular members A1 and A2, when the two semicircular members A1 and A2 are coincident or are mutually spliced (for example when the fastening is realized by means of the two fastening members 501 and 502), the semi-arc-shaped circumcision knives C1 and C2 and also the semi-arc-shaped circumcision knives D1 and D2 form respectively a completely-circular inner edge (or near side edge) and a completely-circular outer edge (or far side edge) through mutual coincidence or overlapping of two corresponding fastening ends;

wherein, the circular inner stapler B is provided with a protruding part E (simply referred to as an inverted V-shaped protruding part E) which has an inverted V-shaped cross section and protrudes outwardly from the circular ring to form a V-shaped recess P (wherein a V-shaped recess P serves as the frenum protecting part), and correspondingly, V-shaped recesses F1 and F2 are arranged on the inner edge of the semi-arc-shaped circumcision knife C1 or C2 of the outer stapler, or on the inner edges of the semi-arc-shaped circumcision knives C1 and D1 or on the inner edges of the semi-arc-shaped circumcision knives C2 and D2, and when the outer stapler is sleeved on the circular inner stapler B, the protruding part E is matched with the V-shaped recess(es) F1 and/or F2;

and wherein the V-shaped recess (es) F1 and/or F2 and the connecting member 505 are in staggered arrangement, that is, the V-shaped recess (es) F1 and/or F2 and the connecting member 505 are arranged at a certain interval. For example, on the semicircular section of the semicircular member A1 or A2, included angles α of one connecting line formed between the lowest point (s) [corresponding to a peak of an inverted V-shaped section of the protruding part E (simply referred to as an inverted V-shaped protruding part E) of B] of the V-shaped recess (es) F1 and/or F2 and the center of the semicircular section and another connecting line formed between a center point (or a center shaft point) of the connecting member 505 and the center of the semicircular section is 15°-165°, preferably, 20°-160°, more preferably, 25°-150°, more preferably, 30°-130°, further preferably, 32°-100°, more further preferably, 32°-90°, for example, 35°, 40°, 45°, 50°, 55°, 60°, 65°, 70°, 75°, 80° and 85°.

Preferably, the V-shaped protruding part E of the inner stapler B inclines or deviates towards the front surface (that is, towards a direction of the base of penis).

Preferably, the near end (that is, close to the direction of the base of penis) of the V-shaped protruding part E of the inner stapler B is provided with a clutching notch H for positioning the frenum.

Preferably, a plurality of bulges 506 are distributed on one side, which is close to the base of penis, of the outer surface of the circular ring of the inner stapler B, and a plurality of bulges 507 are distributed on one side close to the glans penis of penis.

Preferably, a plurality of notches 504 are distributed on the semi-arc-shaped circumcision knives C1 and C2.

A foreskin circumcising method involves inserting the ring (also called the first ring) of the lower (or inner) ring stapler within the foreskin of male patient (e.g. when he lies on his back during a circumcision operation), radially clamping foreskin against circumference of the first ring by the upper (or outer) ring stapler and axially (or annually) cutting the foreskin against the first ring.

Advantages of the Present Application

Compared with the prior art, the first implementation of the present application has the following prominent substantive features and represents a notable progress:

1. The present application is composed of an upper stapler, a lower stapler and a rivet fastening and regulating member, by means of connection using rivets with regulating nuts, the nuts of the rivets are regulated to be capable of moving downwards along lead screws of the rivets under the action of a dedicated torque screwdriver, such that the connection compactness of the upper stapler and the lower stapler is enhanced, and the clinical requirements can be achieved according to different recipients. 2. The present application is simple in structure and convenient to use, can actually achieve purposes of accurate positioning during operation, short duration of operation, and short healing time after operation, can prevent edema, prevent infection and reduce the patient's pain, and can actually reflect the advantage of a disposable circumcision stapler over the conventional operation. 3. Because the frenum can be completely protected, the glans penis and the penis can freely contract and relax, no special discomfort is caused after operation, recent and remote effects are both remarkably superior to various current methods. 4. The present application is designed according to the features of the reproductive organs of the males and the clinical requirements, the circumcision is well standardized to become a standard circumcision operation. 5. The present application creatively design a frenum protecting part which regularly extends a distance along the frenum length direction with the penis as the center to ensure the length of the frenum so as to be used for patients with longer or shorter frenums, and achieves the effects that the patients have no pain, the doctors easily perform the operation, no infection is caused after operation, and no side effects are caused when the circumcision is executed.

Compared with the prior art, the second implementation of the present application has the following features and presents a progress:

Because the frenum protecting part is arranged on the single circumcision knife or two circumcision knives of the upper stapler of the present application, the excision plane in which the frenum protecting part of the upper ring stapler is located and a main body excision plane of upper ring stapler are in the same horizontal plane (when the main body of the upper ring stapler be placed horizontally), but a V-shaped protrusion which is a ring-radial-outward semi-elliptical or triangular radian portion and deviates from main body excision plane to penis's base is arranged on the frenum protecting part of the upper stapler; or the excision plane in which the frenum protecting part of the upper ring stapler is located and the main body excision plane or the upper ring stapler are not in the same horizontal plane (when the main body of the upper ring stapler be placed horizontally), but a V-shaped protrusion which is a ring-radial-outward semi-elliptical or triangular radian portion and deviates from main body excision plane to penis's base is arranged on the frenum protecting part of the upper ring stapler, and still, the main plane of the V-shaped protrusion is parallel to a main plane of a frenum protecting part of the lower ring stapler (when the lower ring stapler and the upper ring stapler are assemblied into a whole); further, because the excision plane in which the frenum protecting part of the lower ring stapler is located and the main body excision plane of the lower ring stapler are on the same horizontal plane when the main body of the lower ring stapler be placed horizontally and this frenum protecting part is provided with or is a V-shaped protrusion as a ring-radial-outward semi-elliptical or triangular radian portion that is protruded outward in a direction perpendicular to the frenum length direction; or the excision plane in which the frenum protecting part of the lower ring stapler is located and the main body excision plane of the lower ring stapler are not on the same horizontal plane when the main body of the lower ring stapler be placed horizontally and this frenum protecting part is provided with or is a V-shaped protrusion as a ring-radial-outward semi-elliptical or triangular radian portion that is protruded outward in a direction perpendicular to the frenum length direction, and still, the main plane of this V-shaped protrusion of lower ring stapler is parallel to the main plane of the frenum protecting part of the upper ring stapler (when the lower ring stapler and the upper ring stapler are assemblied into a whole). Thus, the present application is simple in structure and convenient to use, can ensure and standardize the length of the frenum, can be used for patients with longer or shorter frenums, and achieves the effects that the patients have no pain, the doctors easily perform the operation, no infection is caused after operation, and no side effects are caused when the circumcision is executed. Such an excision manner can ensure the attractiveness of the foreskin after being circumcised, can actually achieve the purpose of effectively protecting the frenum and standardize the circumcision, so that the circumcision can be performed on senile and young patients and patients with shorter frenums.

Compared with the prior art, the third implementation of the present application has the following advantages that such a structure is simple and is convenient to operate, rivet columns are sheared by using a dedicated shear when the device is removed, no pain is caused when the device is removed, and the structure is easily accepted by patients. Such a structure can meet demands of different patients, and is suitable for implementing the circumcision for people in different ages, in particular, the aged and children and patients with shorter frenums.

Compared with the prior art, the fourth implementation of the present application has the following advantages that such a structure described in the present application is a lock catch interdigitating structure with middle shaft fixedly connected, thereby being simple and being convenient to operate, being capable of keeping the balance of two semi-circular rings, causing no pain when the device is removed, and being easily accepted by patients. Such a structure can meet the clinical requirement, and is suitable for implementing the circumcision on patients in different ages.

BRIEF DESCRIPTION OF THE DRAWINGS

The present application will be described below in conjunction with the accompanying drawings and the embodiments:

FIG. 1 is a front perspective view of the present application;

FIG. 2 is a bottom perspective view of the present application;

FIG. 3 is a front perspective view of an upper stapler of the present application;

FIG. 4 is a bottom perspective view of an upper stapler of the present application;

FIG. 5 is a front perspective view of a lower stapler of the present application;

FIG. 6 is a bottom perspective view of a lower stapler of the present application;

FIG. 7 is a front perspective view of a rivet of a circumcision stapler of the present application; and FIG. 8 is a top perspective view of a rivet of a circumcision stapler of the present application.

In FIG. 1 to FIG. 8, 1: upper ring stapler, 2: rivet hole of upper ring stapler; 3: outer excision hole (slit); 4: outer knife of upper ring stapler, 5: anti-skidding bulge of upper ring stapler, 6: the inner ring-knife's anti-skidding groove of the upper ring stapler, 7: frenum protecting part of upper ring stapler, 8: positioning column of upper ring stapler, 9: lower ring stapler, 10: rivet hole of lower ring stapler, 11: inner excision hole (slit); 12: inner knife of lower ring stapler, 13:

anti-skidding bulge of lower ring stapler, 14: the outer ring-knife's anti-skidding groove of the lower ring stapler, 15: frenum protecting part of lower ring stapler, 16: positioning hole of lower stapler, 17: fastening column having a rivet hole, 18: snap ring device having a rivet hole, 19: positioning column of lower ring stapler having a hole (i.e. positioning hole) for inserting of positioning column of upper ring stapler, 20: rivet, 21: rivet boss, 22: rivet lead screw part, 23: rivet screw nut part, 24: rivet cap.

FIG. 9 to FIG. 12 relate to a second implementation of the present application.

Figure 9:
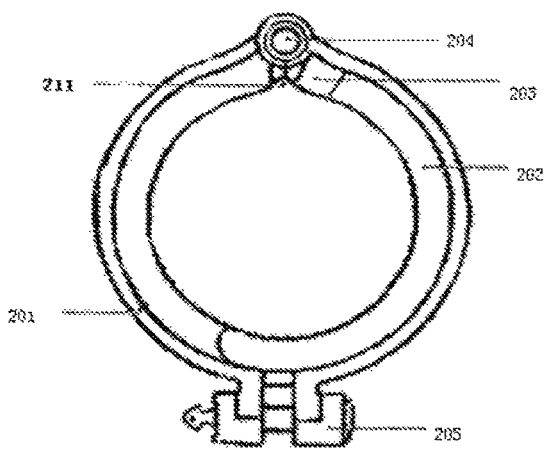
Figure 10:
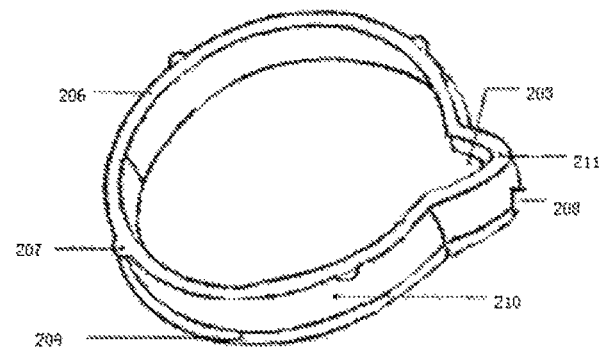
Figure 11:
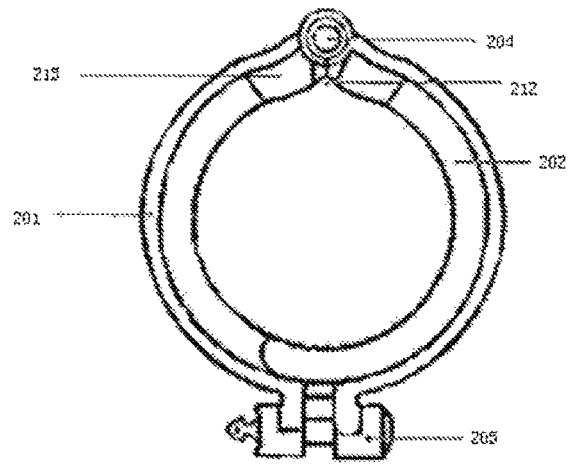
Figure 12:
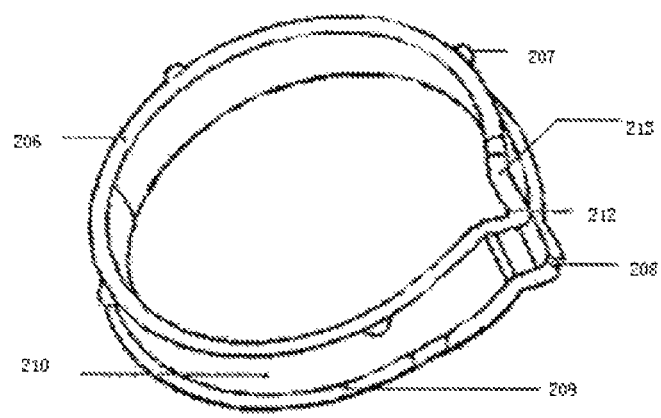

FIG. 9 is a perspective view of a frenum protecting part of an upper stapler which is in the same horizontal excision plane;

FIG. 10 is a perspective view of a frenum protecting part of a lower stapler which is in the same horizontal excision plane;

FIG. 11 is a perspective view of a frenum protecting part of an upper stapler which is not in the same horizontal excision plane; and FIG. 12 is a perspective view of a frenum protecting part of a lower stapler which is not in the same horizontal excision plane.

In FIG. 9 to FIG. 12, 201: upper stapler, 202: excision knife of upper stapler, 203: horizontal frenum protecting part of excision knife of upper stapler, 204: connecting apparatus of upper stapler, 205: regulating apparatus of upper stapler, 206: lower stapler, 207: foreskin anti-skidding bulge of lower stapler, 208: frenum positioning incision, 209: foreskin anti-skidding belt of lower stapler, 210: foreskin excision groove of lower stapler, 211: horizontal-section V-shaped protrusion, 212: arc-shaped-section V-shaped protrusion, 213: arc-shaped-section frenum protecting part of excision knife of upper stapler.

FIG. 13 to FIG. 19 relate to the third implementation of the present application.

Figure 13:
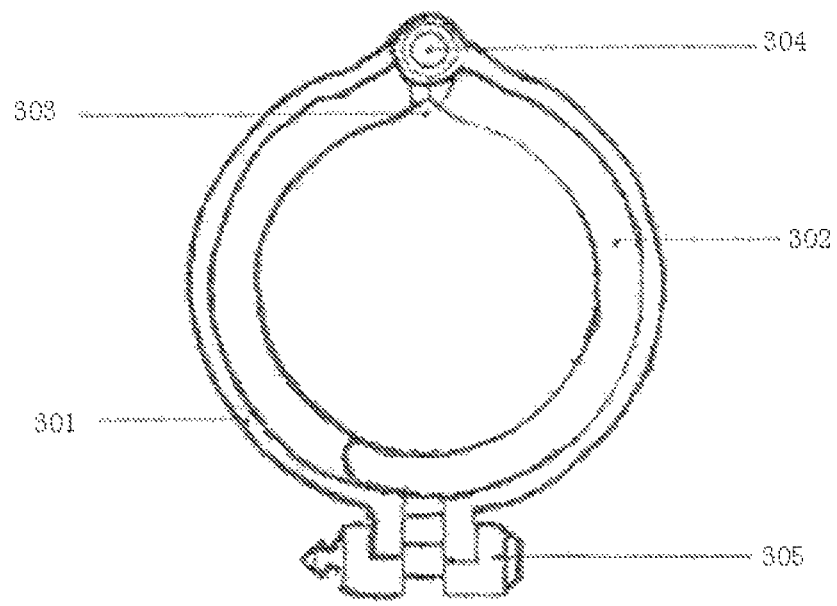
Figure 14:
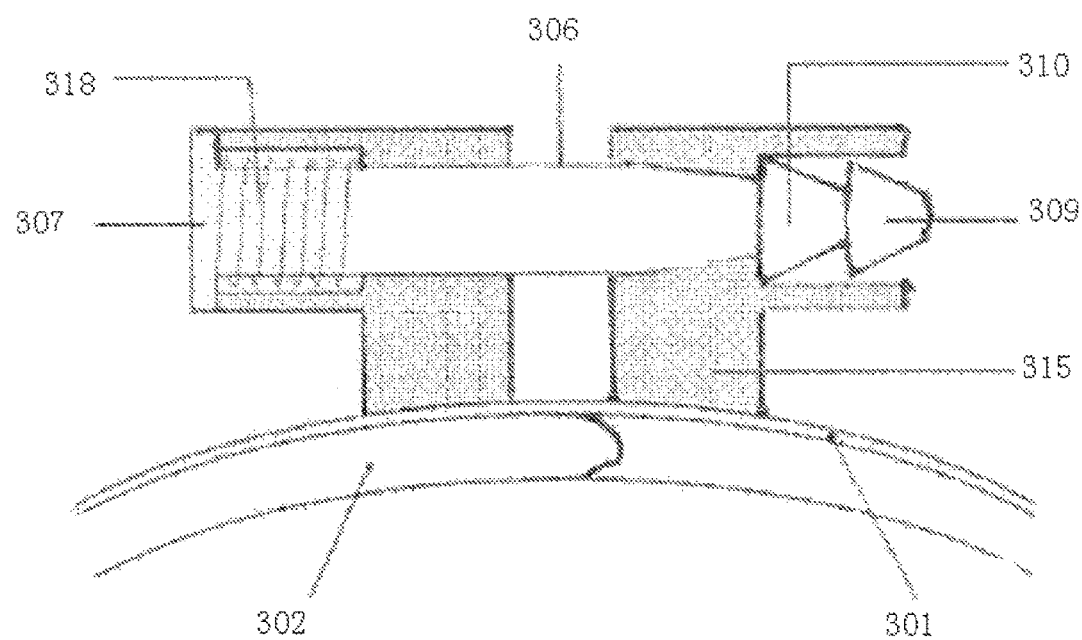
Figure 15:
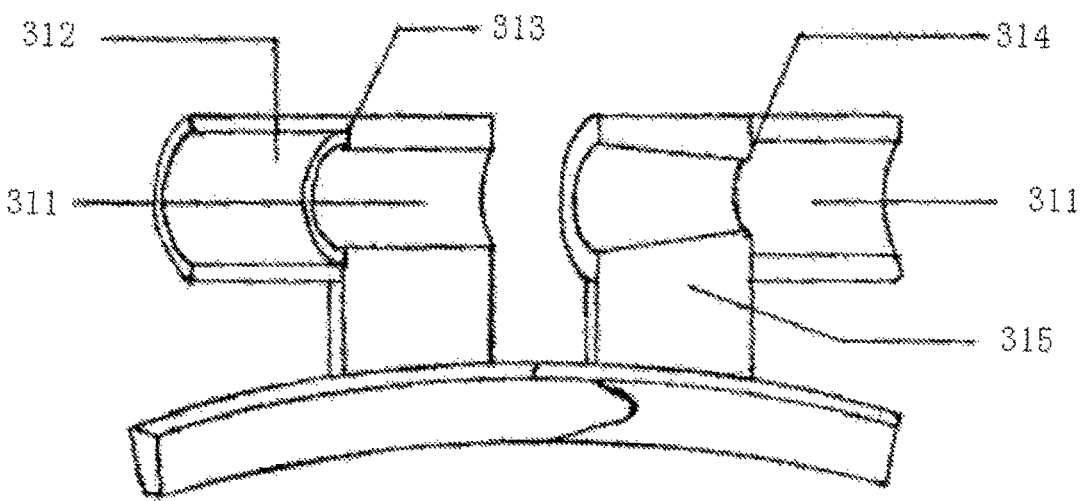
Figure 16:
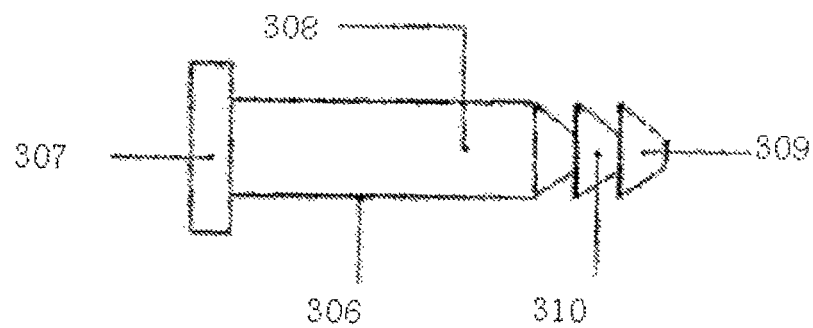
Figure 17:
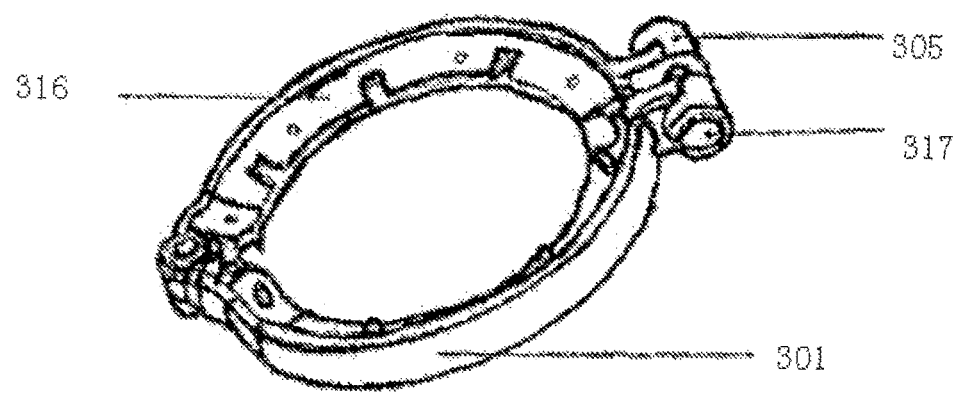
Figure 18:
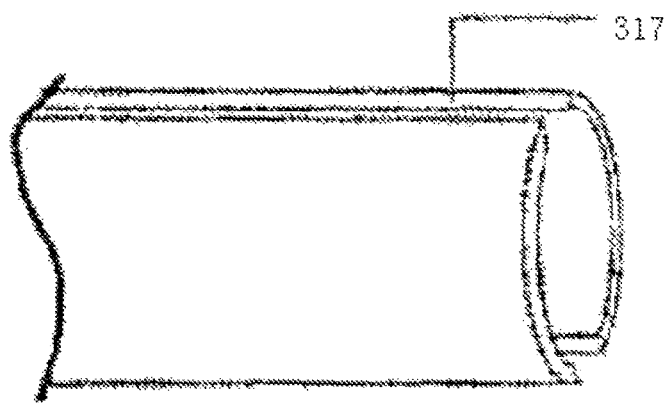
Figure 19:
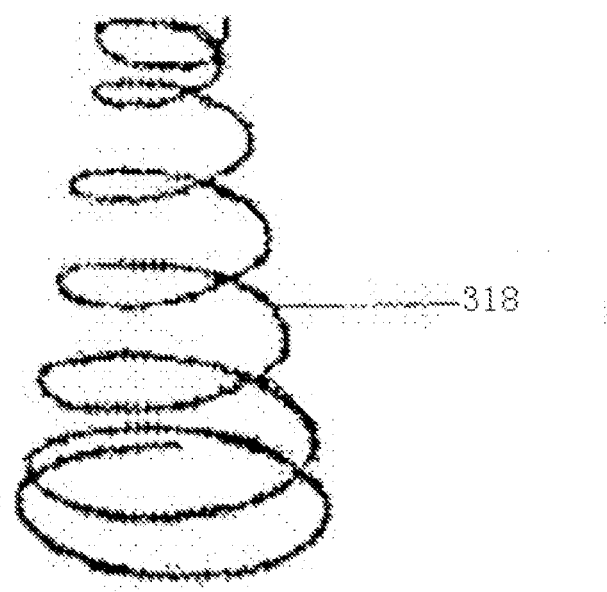

FIG. 13 is a schematic structural diagram showing a position of an upper stapler of the present application;

FIG. 14 is a schematic cross-sectional view of the present application;

FIG. 15 is a perspective cross-sectional view of a structure without rivets, springs, foreskin regulating bosses and foreskin excision bosses of the present application;

FIG. 16 is a perspective view of a rivet of the present application;

FIG. 17 is a bottom perspective view of an upper stapler of the present application;

FIG. 18 is a perspective view of rivet expanding notches of the present application; and FIG. 19 is a schematic structural diagram of a regulating spring of the present application.

In FIG. 13 to FIG. 19, 301: upper stapler, 302: outer knife of upper stapler, 303: frenum protecting part of upper stapler, 304: connecting apparatus of upper stapler, 305: regulating apparatus of upper stapler, 306: rivet, 307: rivet cap; 308: rivet column, 309, boss for regulating foreskin, 310: boss for foreskin excision, 311: rivet channel, 312: spring channel, 313: spring base, 314: rivet boss base, 315: regulating apparatus wall of upper stapler, 316: inner knife of upper stapler, 317: rivet expanding notch, 318: regulating spring.

FIG. 20 to FIG. 23 relate to the fourth implementation of the present application.

Figure 20:
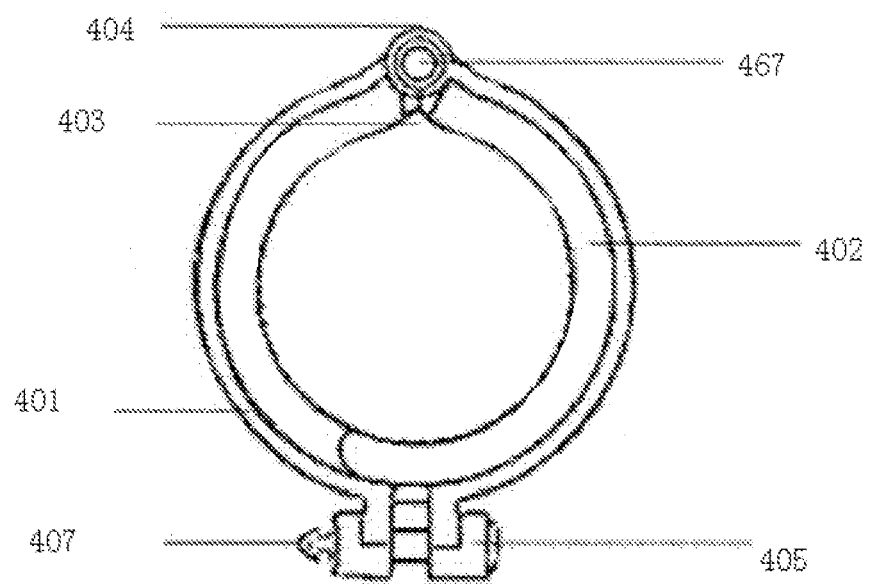
Figure 21:
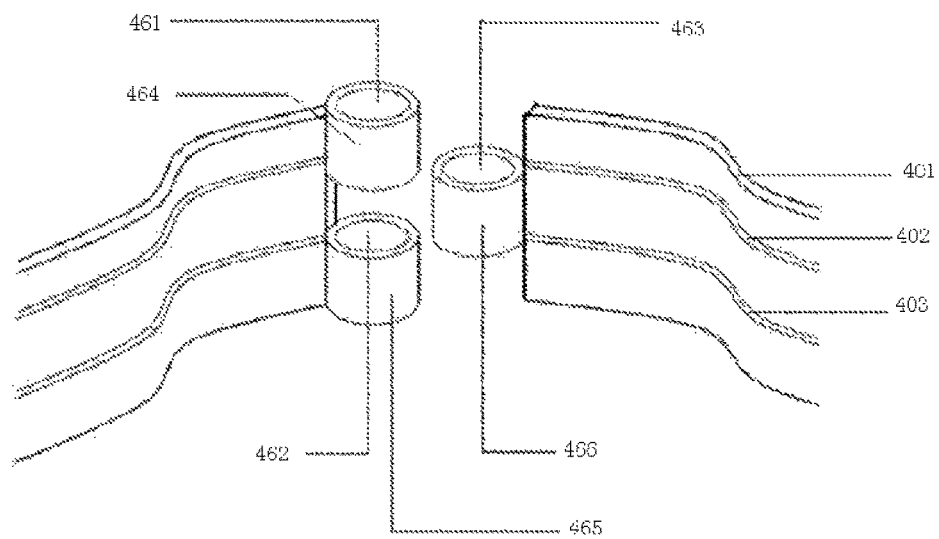
Figure 22:
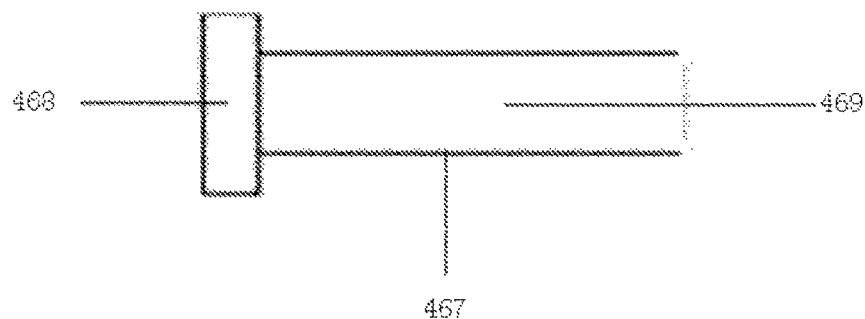
Figure 23:
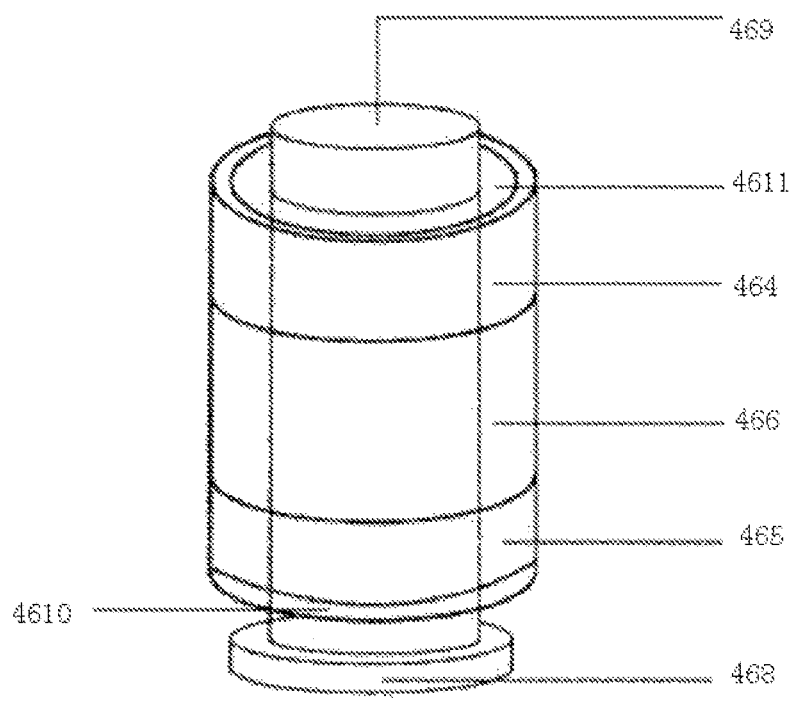

FIG. 20 is a schematic structural diagram showing a position of an upper stapler of the present application;

FIG. 21 is a front perspective view of a structure of the present application;

FIG. 22 is a perspective view of a connecting shaft of the present application; and FIG. 23 is a perspective view of a connecting apparatus of the present application.

In FIG. 20 to FIG. 23, 401: upper stapler, 402: outer knife of upper stapler, 403: inner knife of upper stapler, 404: frenum protecting part of upper stapler, 405: regulating apparatus of upper stapler, 406: connecting apparatus of upper stapler, 461: upper connecting hole, 462: lower connecting hole, 463: middle connecting hole, 464: upper connecting hole wall, 465: lower connecting hole wall, 466: middle connecting hole wall, 467: connecting shaft, 468: connecting shaft cap, 469: connecting shaft column, 4610: lower connecting shaft cap recess, 4611: upper connecting shaft cap recess, 407: rivet.

FIG. 24 to FIG. 33 relate to a sixth implementation of the present application.

Figure 24:
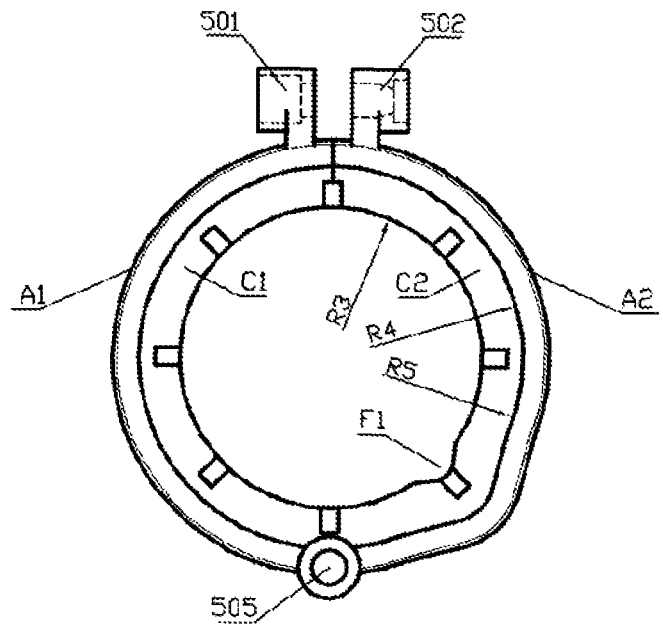
Figure 25:
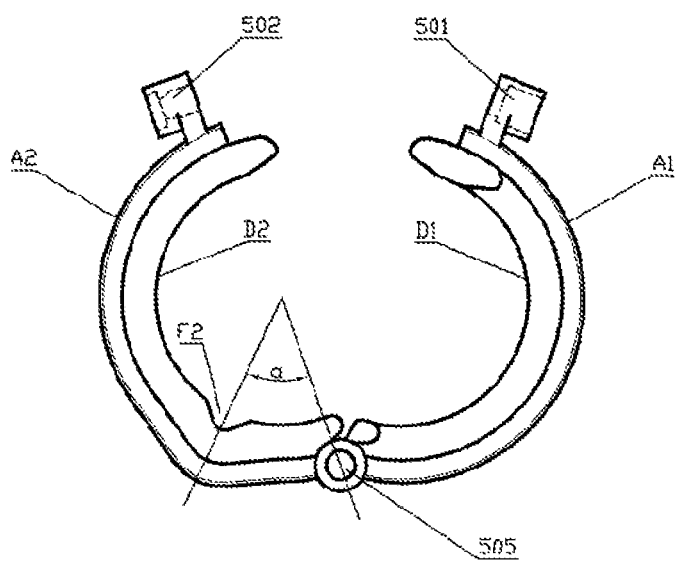
Figure 26:
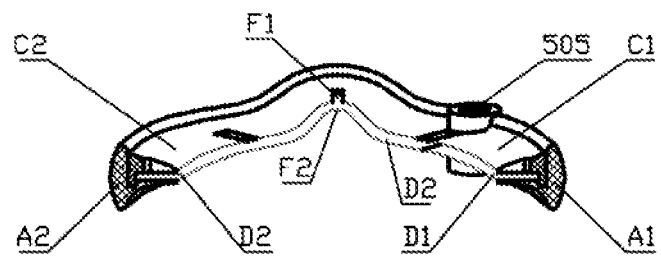
Figure 27:
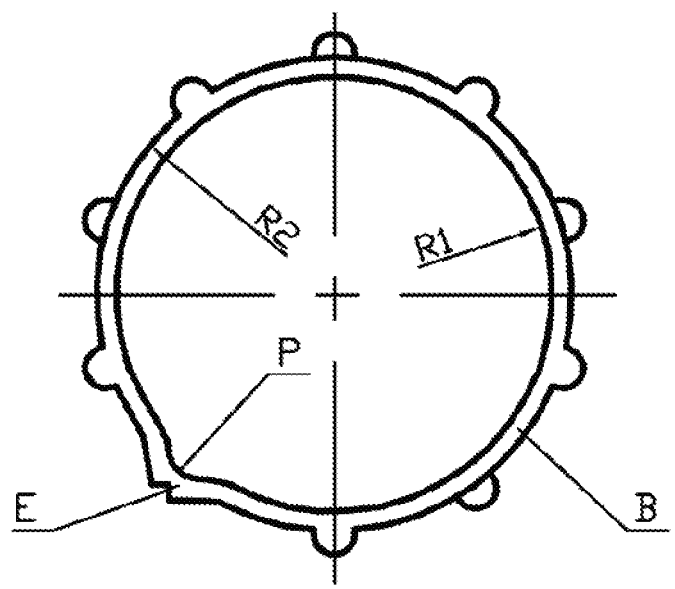
Figure 28:
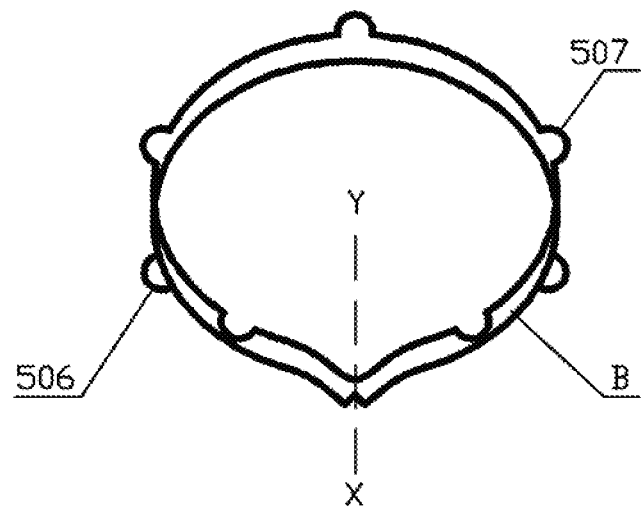
Figure 29:
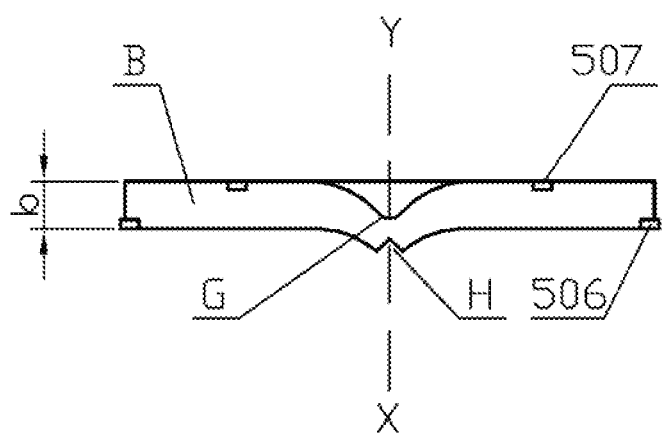
Figure 30:
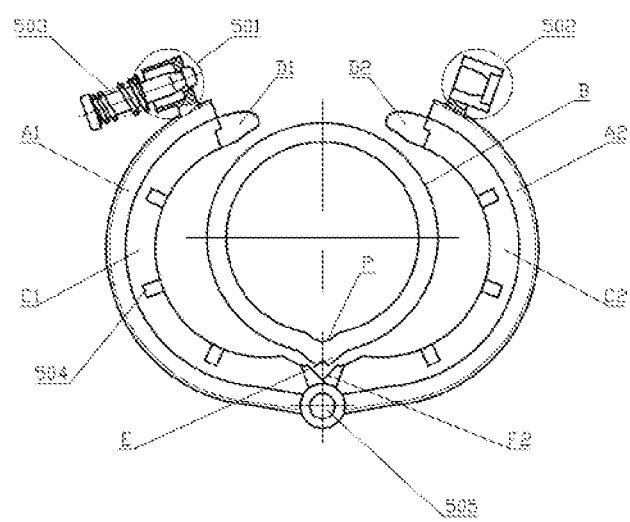
Figure 31:
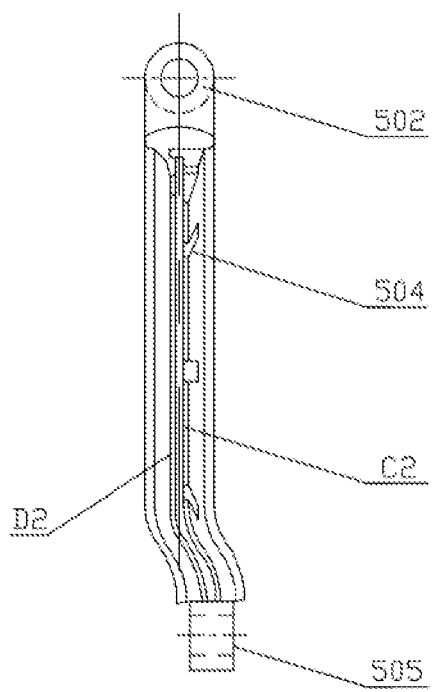
Figure 32:
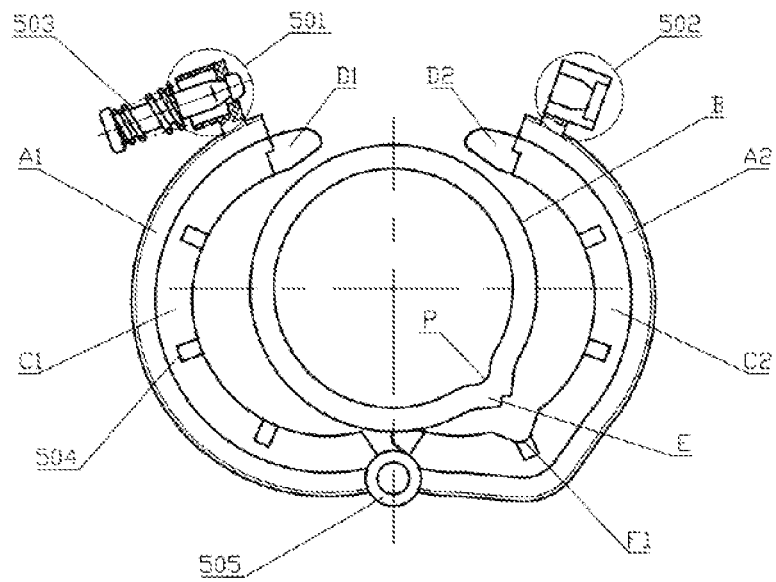
Figure 33:
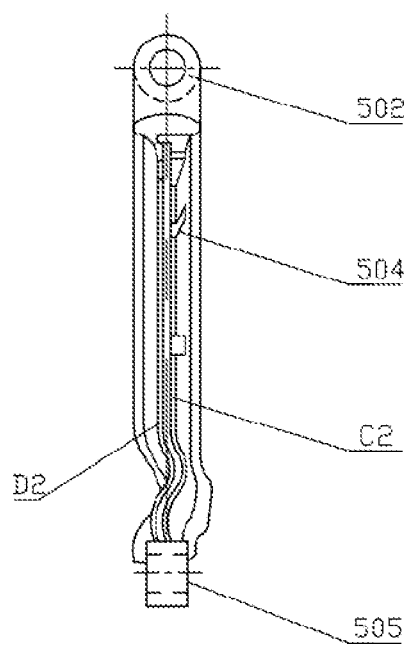

FIG. 24 front view;
FIG. 25 back view;
FIG. 26 cross-sectional view;
FIG. 27 front view of inner ring;
FIG. 28 perspective view of inner ring;
FIG. 29 partial view of frenum protecting part;
FIG. 30 back view of axial assembling;
FIG. 31 side view of axial assembling;
FIG. 32 back view of lateral assembling;
FIG. 33 side view of lateral assembling.

DETAILED DESCRIPTION OF THE APPLICATION

Embodiment 1

Figure 1:
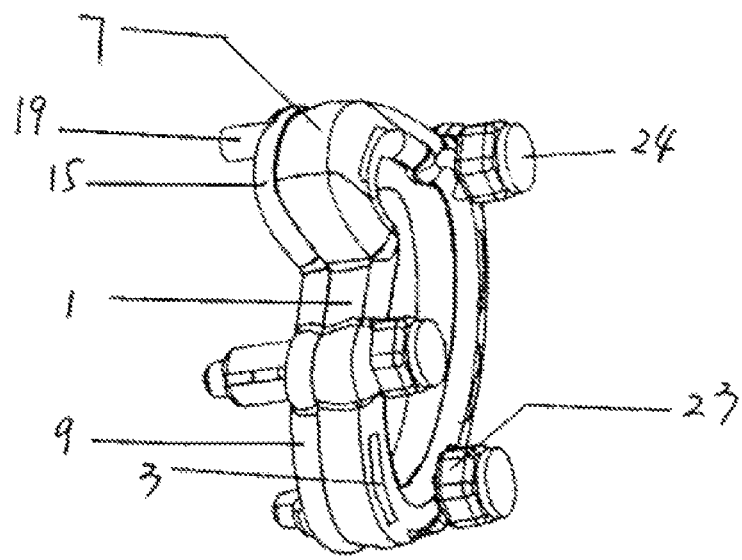
FIG. 1 to FIG. 8 relate to a first implementation of the present application.
Figure 2:
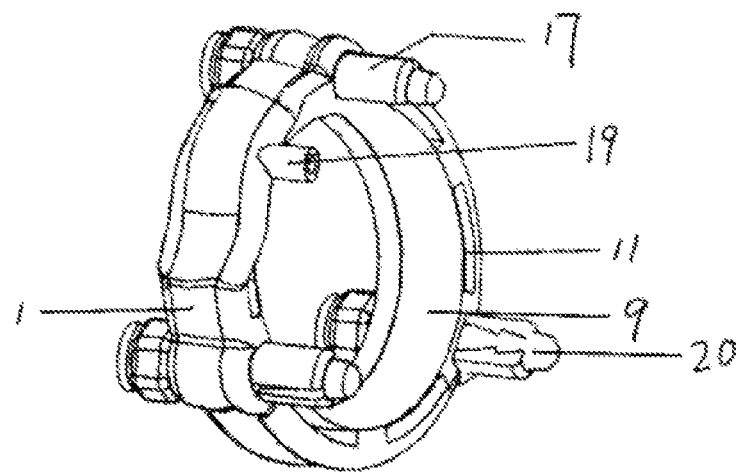

With reference to the accompanying drawings, a disposable circumcision stapler of the present application, as shown in FIG. 1 and FIG. 2, is composed of an upper stapler 1, a lower stapler 9 and a rivet fastening and regulating member, and emphasized in that notches of the whole stapler are not in the same horizontal plane; other than a common main body section, an auxiliary section (also known as an inclined section) intended to protect the frenum is specially designed, that is, a frenum protecting part of the upper stapler and a frenum protecting part of the lower stapler 15, a positioning column 8 of the upper stapler is arranged at the top end of the frenum protecting part 7 of the upper stapler, and connected with a positioning hole 16 of the lower stapler. An inclined angle with a proper radian is formed between the frenum protecting part 7 of the upper stapler and the main body excising plane of upper stapler, and also, an inclined angle with a proper radian is formed between the frenum protecting part (i.e. auxiliary section) 15 of the lower stapler and the main body excising plane of lower stapler; as well as the knife edge on the main body section and the knife edge on the auxiliary section are smoothly connected. Such an excision manner can ensure the attractiveness of the foreskin after being circumcised, and can actually achieve the purpose of effectively protecting the frenum. Such a structure can be used for implementing the circumcision for patients with shorter frenums.

Figure 3:
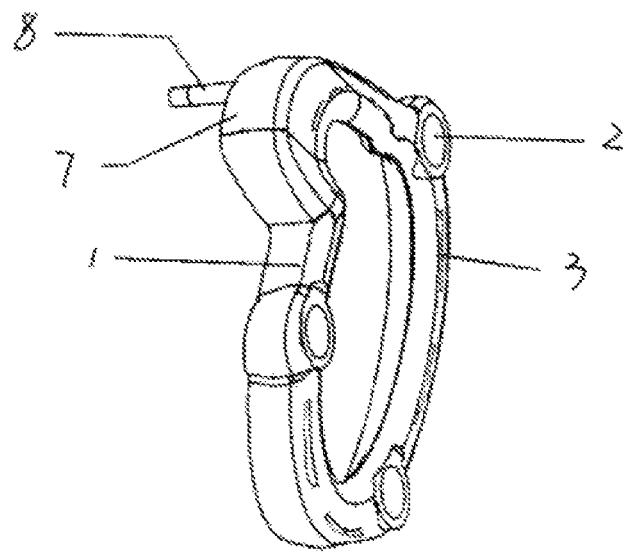
Figure 4:
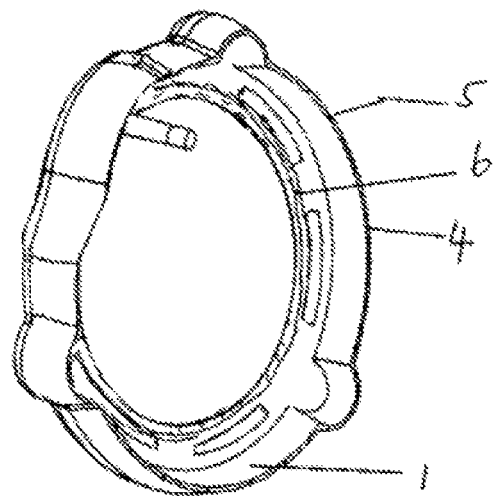
Figure 5:
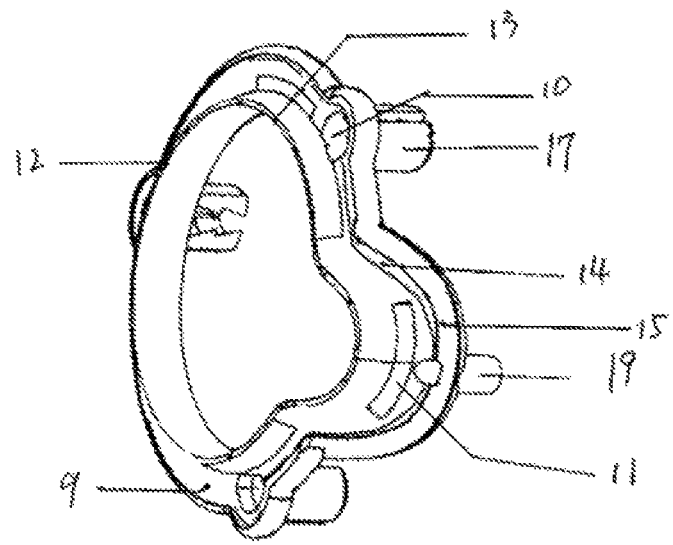
Figure 6:
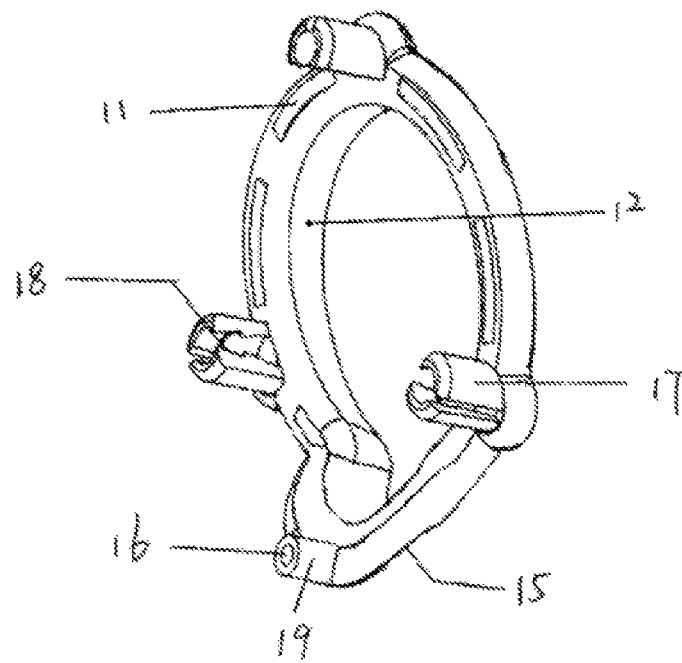
Figure 7:
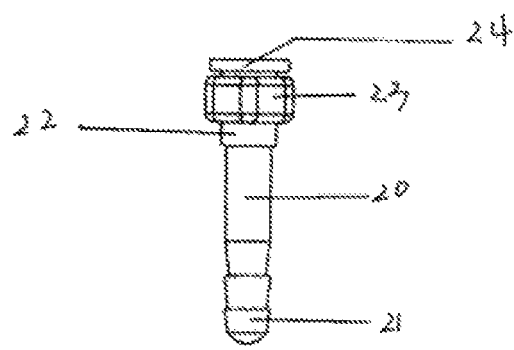
Figure 8:
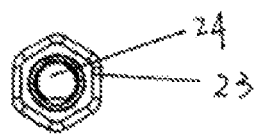

As shown in FIG. 3, FIG. 4, FIG. 5 and FIG. 6, rivet holes 2 of the upper stapler are provided on the upper stapler 1, rivet holes 10 of the lower stapler are provided on the lower stapler 9, the rivet holes of the lower stapler extend to form fixed rivet columns 17, a plurality of outer excision holes 3 are provided on the middle of the upper stapler 1, and correspondingly, a plurality of inner excision holes 11 are provided on the lower stapler 9 as well. As shown in FIG. 3 and FIG. 4, a plurality of anti-skidding bulges 5 of the upper stapler are uniformly arranged on a knife edge of an outer knife 4 of the upper stapler. The outer knife 4 of the upper stapler is a complete auxiliary excision knife, and an inner knife's anti-skidding groove 6 of the upper ring stapler is provided on the inner side of the outer knife of the upper stapler. The outer knife 4 of the upper stapler and the outer knife's anti-skidding groove 14 of the lower stapler are engaged to excise the foreskin. As shown in FIG. 5 and FIG. 6, a plurality of anti-skidding bulges 13 of the lower stapler are uniformly arranged on a knife edge of an inner knife 12 of the lower stapler. An outer knife's anti-skidding groove 14 of the lower stapler is provided on the outer side of the inner knife 12 of the lower stapler, and the anti-skidding bulges 13 are arranged on the inner knife of the lower stapler, thus the foreskin can be effectively prevented from skidding; the inner knife of the lower stapler is a main excision knife, and is engaged with the inner knife's anti-skidding groove 6 of the upper stapler, and a hollow positioning hole 16 of the lower stapler and a positioning column 19 of the lower stapler are arranged at the top end of the frenum protecting part 15 of the lower stapler. The rivet 20 as shown in FIG. 7 and FIG. 8 comprises a rivet boss 21, a rivet lead screw part 22, a rivet screw nut part 23 and a rivet cap 24. The rivet 20 reaches a lower fixed rivet column 17 through the rivet hole 2 of the upper stapler and the rivet hole 10 of the lower stapler, a snap ring 18 is arranged in the fixed rivet column, and the rivet boss 21 is used for connecting the upper stapler and the lower stapler by the plurality of bosses under progressive action of the snap ring. Because of the existence of the individual difference, when the clinical requirement can not be met by means of multiple times of snap-fitting, the rivet screw nut parts play a role of regulating the individual difference. Nuts are regulated by using the rivets to move downwards along a rivet lead screw under the action of a proper force so that the connection compactness between the upper stapler and the lower stapler is enhanced, so that the clinical requirement is met.

A use method during operation comprises: due to individual difference, firstly select a proper stapler, then place the lower stapler on the penis, and perform 4 clock clipping, that is, 12 o'clock clipping, 3 o'clock clipping, 6 o'clock clipping and 9 o'clock clipping (the middle of the back side of the penis is in a 12 o'clock direction, the frenum is in a 6 o'clock direction, the left side is in 3 a o'clock direction, the right side is in a 9 o'clock direction, that is, a clockwise direction) on the foreskin of the penis by using curved forceps; lift the foreskin, firstly fix the curved forceps at 6 o'clock on the positioning hole 16 of the lower stapler; secondly, lift the curved forceps at 12 o'clock, 3 o'clock and 9 o'clock onto respective positions respectively, uniformly spread the foreskin to ensure that an inner plate and an outer plate of foreskin and the frenum direction meet the clinical requirement, then close the upper stapler, insert the rivets respectively, and manually regulate the nuts; thirdly, determine that the distance between the inner plate of the foreskin and the outer plate of the foreskin of the frenum completely meets the clinical requirement, pressurize the rivet caps by using a dedicated torque screwdriver to reach a certain force; and finally, shear excessive foreskin, disinfect the tissues around the foreskin by using iodophor, and end the operation.

Embodiment 2

A manner (2a): a frenum protecting part of a circumcision stapler is in the same horizontal excision plane:

As shown in FIG. 9 and FIG. 10, the designed frenum protecting part of the circumcision stapler in the same horizontal excision plane comprises an upper stapler 201 and a lower stapler 206, wherein the upper stapler 201 is formed by connecting a left semicircular member and a right semicircular member by means of a connecting apparatus 204, the lower stapler 206 and the upper stapler 201 compress to excise excessive foreskin under the action of a regulating apparatus 205 of the upper stapler to cause avascular necrosis of the excessive foreskin; the frenum protecting part has characteristics that a horizontal-section frenum protecting part 203 of an upper stapler excision knife is arranged on a single excision knife 202 of the upper stapler, an excision plane in which the horizontal-section frenum protecting part 203 of the upper stapler excision knife is located and a main body excision plane are in the same horizontal plane, the horizontal-section frenum protecting part 203 of the upper stapler excision knife is provided with V-shaped protrusion 211 which have ring-radial-outward semi-elliptical or triangular radians in a frenum direction on a main body structure, and is also provided with V-shaped protrusion 211 which have ring-radial-outward semi-elliptical or triangular radians in a frenum direction on the lower stapler 206 of the circumcision stapler, and the V-shaped protrusion 211 which have ring-radial-outward semi-elliptical or triangular radians are parallel to the horizontal-section V-shaped protrusion 211 of the upper stapler, a plurality of foreskin anti-skidding bulges 207 of the lower stapler are arranged on one outer edge of the lower stapler, foreskin excision grooves 210 of the lower ring stapler are provided on the ring-radial-outside surfaces of lower ring stapler (in FIG. 12, the foreskin excision grooves 210 is below the foreskin anti-skidding bulges 207), foreskin anti-skidding belts 209 of the lower stapler are arranged on the edge of lower stapler opposite to the foreskin anti-skidding bulges 207 of the lower stapler, and frenum positioning notches 208 are provided on sharp ends of the foreskin anti-skidding belts 209 of the lower stapler, corresponding to the V-shaped protrusion 211 of the horizontal-section frenum protecting part of the lower stapler.

A manner (2b): a frenum protecting part of a circumcision stapler is not in the same horizontal excision plane:

As shown in FIG. 11 and FIG. 12, the designed frenum protecting part, which is not in the same horizontal excision plane, of the circumcision stapler comprises an upper stapler 201 and a lower stapler 206, wherein the upper stapler 201 is formed by connecting a left semicircular member and a right semicircular member by means of a connecting apparatus 204, the lower stapler 206 and the upper stapler 201 compress to excise excessive foreskin under the action of a regulating apparatus 205 of the upper stapler to cause avascular necrosis of the excessive foreskin; the frenum protecting part has characteristics that arc-shaped-section frenum protecting parts 213 of an upper stapler excision knife are arranged on two excision knives 202 of the upper stapler, an excision plane in which the arc-shaped-section frenum protecting parts 213 of the upper stapler excision knife are located and a main body excision plane are not in the same horizontal plane, the arc-shaped-section frenum protecting parts 213 of the upper stapler excision knife are provided with V-shaped protrusion 212 which have ring-radial-outward semi-elliptical or triangular radians in a frenum direction on a main body structure, and also provided with V-shaped protrusion 212 which have ring-radial-outward semi-elliptical or triangular radians in a frenum direction on the lower stapler 206 of the circumcision stapler, and the V-shaped protrusion 211 which have ringradial-outward semi-elliptical or triangular radians are parallel to the arc-shaped-section V-shaped protrusion 212 of the upper stapler, a plurality of foreskin anti-skidding bulges 207 of the lower stapler are arranged on one outer edge of the lower stapler, foreskin excision grooves 210 of the lower stapler are provided on the inner side surfaces of the foreskin anti-skidding bulges 207, foreskin anti-skidding belts 209 of the lower stapler are arranged on edges opposite to the foreskin anti-skidding bulges 207 of the lower stapler, and frenum positioning notches 208 are provided on sharp ends of the foreskin anti-skidding belts 209 of the lower stapler, corresponding to the V-shaped protrusion 211 of the arc-shaped-section frenum protecting part of the lower stapler.

Embodiment 3

With reference to FIG. 13 to FIG. 19, as shown in FIG. 13 and FIG. 17, one ends of two irregular semicircular upper staplers 301 of a disposable circumcision device where the frenum exists are connected together by means of a connecting apparatus 304, the other ends of the two irregular semicircular upper staplers are connected by means of a regulating apparatus 305 under the action of a rivet 306 and a regulating spring 318, an outer knife 302 and an inner knife 316 as well as frenum protecting parts 303 of the upper staplers are arranged between two ends of the upper staplers 301; as shown in FIG. 13, FIG. 14, FIG. 15, FIG. 17 and FIG. 18, the regulating apparatus 305 is arranged at the opened ends of the back surfaces of the two semicircular outer sides of the upper staplers, wherein one opened end is connected to one end of the regulating apparatus 305 composed of a regulating member wall 315, a rivet channel 311, a spring channel 312 and a spring base 313, the other opened end is connected to the other end of the regulating apparatus 305 composed of the regulating member wall 315, a rivet channel 311, a rivet boss base 314 and a rivet expanding notch 317. As shown in FIG. 13, FIG. 14, FIG. 16 and FIG. 17, the rivet 306 is composed of a rivet column 308, a rivet cap 307, a foreskin regulating boss 309 and a foreskin excision boss 310, and trunk of the rivet may has a cylindrical shape, a square-column shape or a cylindrical and square-column mixed shape. As shown in FIG. 14 and FIG. 19, the regulating spring 318 is sleeved on the rivet column 308 of the rivet 306, and is a tower type compression spring or scroll compression spring; after the foreskin regulating boss 309 of the rivet 306 passes through the rivet channel 311, the spring channel 312 and the spring base 313 at one side to the rivet channel 311 and the rivet boss base 314 at the other side, when the foreskin regulating boss 309 reaches the rivet boss base 314, that is, when the foreskin regulating boss is blocked on the rivet boss base 314 for a first time, the regulating spring 318 correspondingly reaches a position in which the spring base 313 is located through the spring channel 312, at this moment, doctors may freely regulate the foreskin, pressurizes the rivet cap 307 by using one hand to enable the foreskin excision boss 310 reaches the position in which the rivet boss base 314 is located again, that is, the foreskin excision boss 310 is blocked on the rivet boss base 314 for a second time when the operation requirement is met. Thus, by means of two times of blocking, the clinical requirement is met. Such a manner can be commonly used for various necessary regulations and excisions.

Embodiment 4

With reference to the accompanying drawings, as shown in FIG. 20, a disposable circumcision device is composed of two irregular semicircular upper staplers 401, one ends of the two upper staplers 401 are opened ends, regulating apparatuses 405 are arranged on the opened ends, the regulating apparatuses 405 of the upper staplers are connected by means of a rivet 407; frenum protecting parts 404 of the upper staplers 401 are arranged at the other ends of the upper staplers 401, tops of the frenum protecting parts are used for movably connecting the two irregular semicircular upper staplers 1 into a whole by means of connecting apparatuses 406 under the action of a connecting shaft 467, outer knives 402 of the upper staplers, inner knives 403 of the upper staplers and frenum protecting parts 404 of the upper staplers are arranged on the upper staplers 401; as shown in FIG. 21, the connecting apparatuses 406 are arranged at opened ends of the back surfaces of the two semicircular outer sides of the upper staplers, that is, outer side edges of the frenum protecting parts 404, wherein an upper connecting ring consisting of an upper connecting hole 461 and an upper connecting hole wall 464 and a lower connecting ring consisting of a lower connecting hole 462 and a lower connecting hole wall 465 are arranged on the opened end at one side; a middle connecting ring consisting of a middle connecting hole 463 and a middle connecting hole wall 466 is arranged on the opened end at the other side; all connecting holes of the upper connecting ring, the middle connecting ring and the lower connecting ring are equal in inner diameter, all connecting hole walls of the upper connecting ring, the middle connecting ring and the lower connecting ring are equal in outer diameter, the heights of the upper connecting ring and the lower connecting ring are equal, the height of the middle connecting ring is greater than those of the upper connecting ring and the lower connecting ring, and heights of the upper connecting ring, the middle connecting ring and the lower connecting ring may be equal as well. Meanwhile, the middle connecting ring is embedded and clamped between the upper connecting ring and the lower connecting ring; the upper connecting ring, the middle connecting ring and the lower connecting ring are movably connected into a whole by means of a connecting shaft 467 inserted in connecting holes of the upper connecting ring, the middle connecting ring and the lower connecting ring in a penetrating manner. The connecting shaft 467 as shown in FIG. 22 is composed of a connecting shaft cap 468 and a connecting shaft column 469 connected with the connecting shaft cap. FIG. 23 shows an assembling process of connecting apparatuses 406 of the upper staplers, that is, the connecting shaft column 469 reaches a lower connecting shaft cap recess 4610 of the lower connecting hole 462 through the lower connecting hole 462, the middle connecting hole 463, the upper connecting hole 461 and the connecting shaft cap 468, at this moment, the connecting shaft cap 468 is level with the outer side surface of the lower connecting hole 462; the connecting shaft column 469 reaches an upper connecting shaft cap recess 4611 of the upper connecting hole 461, and then the front end of the connecting shaft column 469 is cauterized by using a dedicated screw cap end socket or using soldering iron. By applying such a lock catch interdigitating manner, and adopting a middle shaft fixed-connecting method, such a structure is simple and is convenient to operate, may keep the balance of two semicircular rings, causes no pain when the device is removed, which can completely meet the clinical requirements.

Embodiment 5

FIG. 24 to FIG. 33 show a sixth implementation of the present application.

The circumcision stapler or circumcision device of the present application may be made of a medical plastic material or nanometer material or light stainless steel material; it will be apparent to those skilled in the art that various changes may be made without departing from the scope of the present application, all changes will be considered to be similar and are included within the scope of this patent.

The invention claimed is:

1. A circumcision stapler kit comprising:
   an upper ring stapler comprising one or two outer ring-knife(s) on a lower-and-outer side circumference of the upper ring stapler;
   a lower ring stapler comprising an inner ring-knife on an upper-and-inner side circumference of the lower ring stapler; and
   a rivet fastening and regulating member comprising a rivet,
   wherein the upper ring stapler further comprises:
      an anti-skidding groove into which the inner ring-knife of the lower ring stapler will be fitted,
      anti-skidding bulges on an edge of the one or two outer ring-knife(s),
      a frenum protecting part which is a part of a ring of the upper ring stapler, the frenum protecting part of the upper ring stapler is or has a ring-radial-outward semi-elliptical portion or a triangular radian portion, and
      a plurality of rivet holes arranged on the upper ring stapler,
      wherein a foreskin-cutting plane of a portion of the one or two outer ring knife(s) which is in the frenum protecting part of the upper ring stapler and a foreskin-cutting plane of a remaining main portion of the one or two outer ring-knife(s) are not in the same horizontal plane when a main body of the upper ring stapler is placed horizontally,
   wherein the lower ring stapler further comprises:
      an anti-skidding groove into which the one or two outer ring-knife(s) of the upper ring stapler will be fitted,
      rivet fastening columns, each rivet fastening column comprising a snap ring with a rivet hole, and each rivet fastening column including a rivet hole of the lower ring stapler,
      anti-skidding bulges on an edge of the inner ring knife, and
      a frenum protecting part which is a part of a ring of the lower ring stapler arranged on the lower ring stapler, the frenum protecting part of the lower ring stapler being or having a ring-radial-outward semi-elliptical portion or triangular radian portion, and the frenum protecting part of the lower ring stapler corresponding to or engaging with a radian of the frenum protecting part of the upper ring stapler,
      wherein a foreskin-cutting plane of a portion of the inner ring-knife which is in the frenum protecting part of the lower ring stapler and a foreskin-excision plane of a remaining main portion of the inner ring-knife are not in the same horizontal plane when a main body of the lower ring stapler is placed horizontally,
   wherein the upper ring stapler and the lower ring stapler are assembled as a kit by the rivet of the rivet fastening and regulating member penetrating through one of the rivet holes of the upper ring stapler, one of the rivet fastening columns, one of the rivet holes of the lower ring stapler, and the rivet hole of the snap ring of the one of the rivet fastening columns, and
   wherein the one or two outer ring-knife(s) of the upper ring stapler engage with the anti-skidding groove of the lower ring stapler, the inner ring-knife of the lower ring stapler engages with the anti-skidding groove of the upper ring stapler, and a fixation provided by the anti-skidding bulges of the upper ring stapler allow the upper ring stapler and the lower ring stapler to be tightly connected so as to engage with and circumcise a foreskin.

2. The circumcision stapler kit according to claim 1,
   wherein the rivet holes of the plurality of rivet holes of the upper ring stapler penetrate through the upper ring stapler and are distributed on a corresponding main plane of the upper ring stapler,
   wherein the one or two outer ring-knife(s) of the upper ring stapler are positioned at an outer edge of an outside of the upper ring stapler, the one or two outer ring-knife(s) being auxiliary excision knife(s), annular three-dimensional multi-faced excision knife(s), and complete annular three-dimensional multi-faced arc-shaped knife(s),
   wherein the anti-skidding groove of the upper ring stapler is a complete concave groove and is parallel to the one or two outer ring-knife(s), a certain gap being arranged between an outside of the complete concave groove and the one or two outer ring-knife(s) of the upper ring stapler, a plurality of narrow hollow slits being arranged between the certain gap and an upper side of the upper ring stapler, the plurality of narrow hollow slits forming outer excision holes or slits.

3. The circumcision stapler according to claim 2,
   wherein the rivet holes of the lower ring stapler penetrate through the lower ring stapler, the rivet holes of the lower ring stapler corresponding to the rivet holes of the upper ring stapler,
   wherein each of the rivet fastening columns comprises a hollow tubular column formed by one of the rivet holes of the lower ring stapler, the hollow tubular column extending outwards from a side of a main plane of the lower ring stapler that is configured to face towards a base of a penis, a distal end of each of the rivet fastening columns being opened so that the hallow tubular column is divided into a left part and a right part, and the snap ring of each rivet fastening column being arranged in the hollow tubular column of said rivet fastening column,
   wherein the inner ring-knife of the lower ring stapler is a main excision knife and a complete annular three-dimensional excision knife having a cambered edge over the frenum protecting part,
   wherein the anti-skidding groove of the lower ring stapler is a complete concave groove, a certain gap being arranged between an inside of the complete concave groove and the inner ring-knife of the lower ring stapler, and a plurality of narrow hollow slits being arranged between the certain gap of the lower ring stapler and a lower side of the lower ring stapler, the plurality of narrow hollow slits forming inner excision holes or slits that correspond to the outer excision holes or slits of the upper ring stapler.

4. The circumcision stapler according to claim 2,
   wherein the frenum protecting part of the upper ring stapler is positioned at a lower side of the upper ring stapler when the circumcision stapler kit is placed on a man's penis with a frenum direction being downward, the frenum protecting part of the upper ring stapler extending forward along a length direction of a frenum with the penis as the center, and wherein a top end of the ring-radial-outward semi-elliptical portion or the triangular radian portion is provided with a frenum positioning column, or reserved with a frenum positioning opening.

5. The circumcision stapler according to claim 2, wherein the rivet of the rivet fastening and regulating member comprises a rivet boss, a rivet lead screw part, a rivet cap, and a rivet screw nut, wherein the rivet boss is positioned at a front end of the rivet and is formed by two successive boss parts with different sizes with a space provided between the successive boss parts, the rivet lead screw part is positioned at a rear end of the rivet and is threaded, and the rivet cap is positioned at a tail end of the rivet lead screw part to prevent the rivet screw nut from slipping, and wherein the rivet screw nut is a gear-shaped or polygonal screw nut and matches with the rivet lead screw part in a nesting manner.

6. The circumcision stapler kit according to claim 1, wherein the frenum protecting part of the upper ring stapler is positioned at a lower side of the upper ring stapler when the circumcision stapler kit is placed on a man's penis with a frenum direction being downward, the frenum protecting part of the upper ring stapler extending forward along a length direction of a frenum with the penis as the center wherein a top end of the ring-radial-outward semi-elliptical portion or triangular radian portion is provided with a frenum positioning column, or reserved with a frenum positioning opening.

7. The circumcision stapler according to claim 6, wherein the frenum protecting part of the lower ring stapler is positioned at a lower side of the lower ring stapler when the circumcision stapler kit is placed on the man's penis with a frenum direction being downward, the frenum protecting part of the lower ring stapler extending forward along the length direction of the frenum with the penis as the center, and wherein a top end of the ring-radial-outward semi-elliptical portion or the triangular radian portion of the lower ring stapler is provided with a hollow tubular column which corresponds to the frenum positioning column.

8. The circumcision stapler according to claim 1, wherein the rivet of the rivet fastening and regulating member comprises a rivet boss, a rivet lead screw part, a rivet cap, and a rivet screw nut, wherein the rivet boss is positioned at a front end of the rivet and is formed by two successive boss parts with different sizes with a space provided between the successive boss parts, the rivet lead screw part is positioned at a rear end of the rivet and is threaded, and the rivet cap is positioned at a tail end of the rivet lead screw part to prevent the rivet screw nut from slipping, and wherein the rivet screw nut is a gear-shaped or polygonal screw nut and matches with the rivet lead screw part in a nesting manner.

\* \* \* \* \*